US00PP08678P

United States Patent [19]

Austin

[11] Patent Number: Plant 8,678

[45] Date of Patent: Apr. 12, 1994

[54] ROSE PLANT 'AUSWALKER'

[75] Inventor: David C. H. Austin, Albrighton, England

[73] Assignee: David Austin Roses Limited, Albrighton, England

[21] Appl. No.: 954,960

[22] Filed: Sep. 30, 1992

[51] Int. Cl.[5] ..... A01H 5/00

[52] U.S. Cl. ..... Plt./1

[58] Field of Search ..... Plt. 1, 24

*Primary Examiner*—Howard J. Locker
*Assistant Examiner*—E. F. McElwain
*Attorney, Agent, or Firm*—Klarquist, Sparkman, Campbell, Leigh and Whinston

[57] ABSTRACT

A shrub rose variety having bright yellow flowers, quartered flowers, upright growth, and strong fragrance.

1 Drawing Sheet

The present invention relates to a new and distinct variety of shrub rose plant of the Rosa hybrida class which was originated by me by crossing the variety Graham Thomas, with the variety Yellow Button.

The primary objective of this breeding was to produce a new rose variety having yellow, quartered, scented flowers on a bushy plant which repeatedly flowers. The objective was substantially achieved along with other desirable improvements as evidenced by the following unique combination of characteristics which are outstanding in the new variety and which distinguish it from its parents, as well as from all other varieties of which I am aware:

1. Bright yellow flowers;
2. Quartered flowers;
3. Upright growth; and
4. Strong fragrance.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated.

Parentage:

*Seed parent.*—Graham Thomas.

*Pollen parent.*—Yellow Button.

Classification:

*Botanical.*—Rosa hybrida.

*Commercial.*—Shrub.

FLOWER

Observations made from specimens grown in a garden environment in Albrighton, Wolverhampton, England in August 1991.

Blooming habit: Recurrent.

Bud:

*Size.*—The bud is about ¾ long when the petals start to unfurl.

*Form.*—Globular, pointed ovoid.

*Color.*—When sepals first divide, the bud color is yellowish green 1B8 to light yellow 3A5. When half blown, the upper sides of the petals are chrome yellow 3A8 at the base, paling to milk white 1A2 at the top; and the lower sides of the petals are vivid yellow 3A7 at the base, paling to milk white 1A2 at the top.

*Sepals.*—Color: Apple green 29C7 with reddish blush. Surface texture: Leathery. There are three normally appendaged sepals. There are two unappendaged sepals with hairy edges.

*Receptacle.*—Color: Greyish green. Shape: Goblet shaped. Size: Small, about ¼×¼". Surface: Hairy.

*Peduncle.*—Length: Medium, averaging about 1½". Surface: Smooth, slightly tomestose. Color: Medium green, reddish brown blotching. Strength: Erect.

Bloom:

*Size.*—Medium. Average open size is 2½"-3¼" in diameter.

*Borne.*—Singly, several together in clusters of up to 5 flowers.

*Stems.*—Medium. Average length is about 24 to 36 inches.

*Form.*—When first open: Cupped. Permanence: Flattens. Outer petals curl back.

*Petalage.*—Number of petals under normal conditions: 170.

*Color.*—The upper side of the petals is pale yellow 2A3 at the outer edge, deepening to light yellow 3A5 at the base. The reverse side of the petals is pale yellow 2A3 at the outer edge, deepening to pastel yellow 3A4 at the base. The major color on the upper side is pale yellow 2A3.

*Variegations.*—None.

*Discoloration.*—The general tonality at the end of the first day: Paler. At the end of the third day, the majority of the petals are milk white 1A2 at the outer edge, changing to pale yellow 2A3 at the base.

*Fragrance.*—Slight.

Petals:

*Texture.*—Thin, soft and silky.

*Shape.*—Round, apex retuse.

*Form.*—Tips are slightly recurved, edges slightly quilled.

*Arrangement.*—Quartered, with no petaloids in the center.

*Persistence.*—Petals drop off cleanly before drying.

*Lastingness.*—On the plant: About 7 to 10 days. As a cut flower: About 5 to 7 days.

Reproductive parts:

*Anthers.*—Size: Medium. Quantity: Few (5). Color: Yellow. Arrangement: Regular around styles.

*Filaments.*—Color: White.

*Pollen.*—Color: Gold yellow.

*Styles.*—Color: Greenish white with some brownish red streaks.

*Stigmas.*—Color: Greenish white.

Form: Shrub.

Growth: Medium, upright.

Height: 36 to 42 inches.

Foliage: Number of leaflets on normal mid-stem leaves: 7.

*Size.*—Medium, about 2" long × 1½ wide.

*Quantity.*—Normal.

*Color.*—New foliage: Deep green 29D8. Ox blood red 9E7 at the margins. Old foliage: Dark green 29F8.

Leaflets:

*Shape.*—Pointed oval.

*Texture.*—Upper side: Leathery.

*Edge.*—Serrated.

*Serration.*—Single, small.

*Petiole rachis.*—Color: Dark green 29F8 with violet brown 10F8 blush.

*Petiole underside.*—With prickles, 0 to 2 per node.

*Stipules.*—Medium, serrated, about ¼ × ¾".

*Disease resistance.*—Resistant to mildew and blackspot under normal growing conditions in Albrighton, Wolverhampton, England.

Wood:

*New wood.*—Color: Apple green 29C7, with reddish tinge. Bark: Smooth.

*Old wood.*—Color: Deep green 29D7. Bark: Smooth.

Prickles:

*Quantity.*—On main canes from base: Few to ordinary. On laterals from main canes: Few.

*Form.*—Medium, hooked downward.

*Color when young.*—Brownish red 10D7 at the base, paling to pompein yellow 5C6 at the tip.

*Position.*—Evenly distributed.

Small prickles:

*Quantity.*—On main stalks: None. On laterals: None.

I claim:

1. A new and distinct variety of shrub rose plant of the Rosa hybrida class, substantially as herein shown and described, characterized particularly as to novelty by the unique combination of its bright yellow flowers, quartered flowers, upright growth, and strong fragrance.

* * * * *

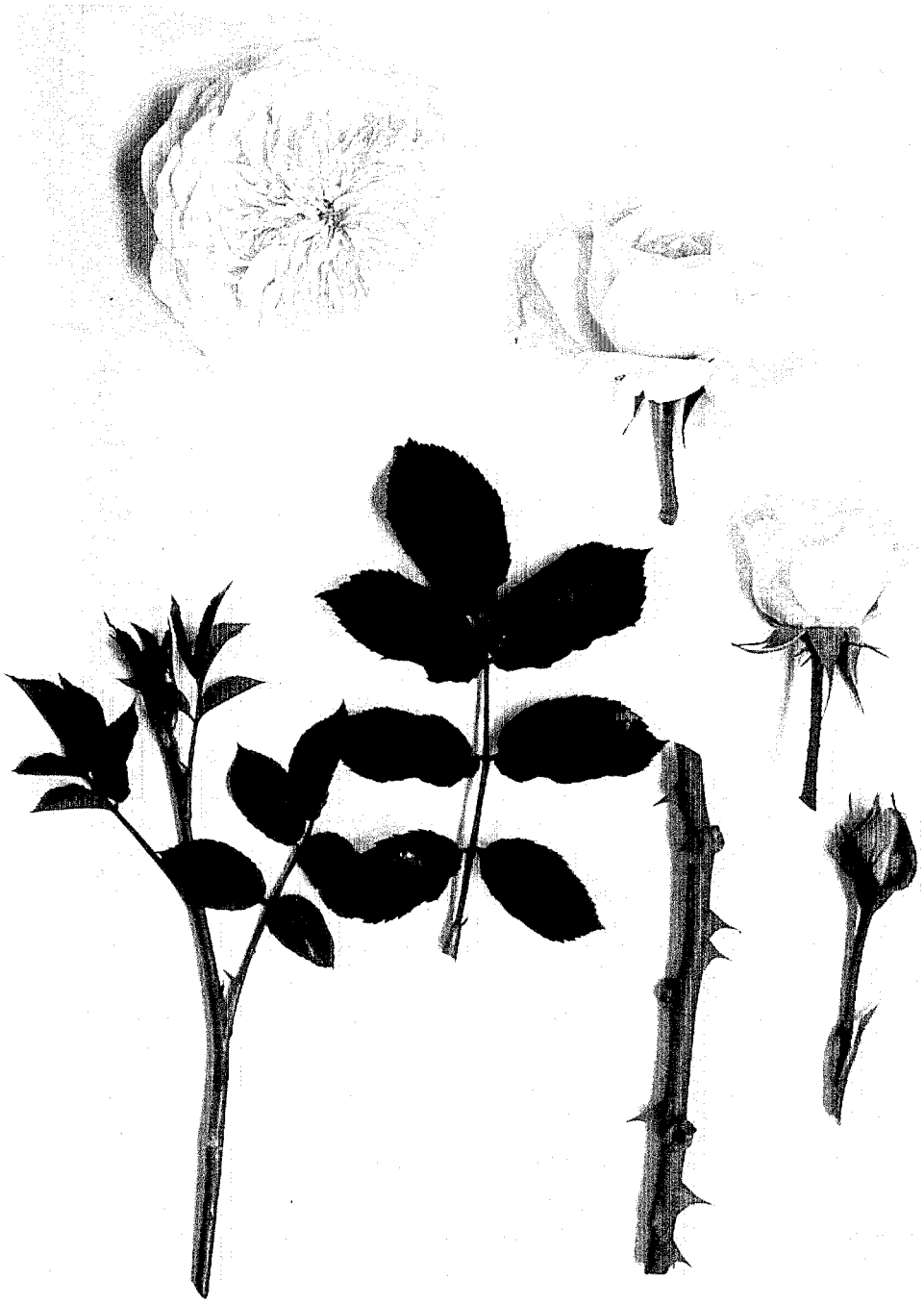
AL Swalker